(12) United States Patent
Ni et al.

(10) Patent No.: US 7,202,066 B2
(45) Date of Patent: Apr. 10, 2007

(54) COMBINATION OF A GROWTH FACTOR AND A PROTEASE ENZYME

(75) Inventors: Yawei Ni, College Station, TX (US); Kenneth M. Yates, Grand Prairie, TX (US)

(73) Assignee: Carrington Laboratories, Inc., Irving, TX (US)

( * ) Notice: Subject to any disclaimer, the term of this patent is extended or adjusted under 35 U.S.C. 154(b) by 0 days.

(21) Appl. No.: 10/059,627

(22) Filed: Jan. 29, 2002

(65) Prior Publication Data

US 2003/0147876 A1    Aug. 7, 2003

(51) Int. Cl.
*C12N 9/00* (2006.01)
(52) U.S. Cl. ...................................... 435/183
(58) Field of Classification Search ................. 435/183
See application file for complete search history.

(56) References Cited

U.S. PATENT DOCUMENTS

| | | | |
|---|---|---|---|
| 4,996,050 A * | 2/1991 | Tsukada et al. | |
| 5,589,451 A * | 12/1996 | Wilson | |
| 5,631,011 A | 5/1997 | Wadstrom | |
| 5,677,278 A | 10/1997 | Gospodarowicz et al. | |
| 5,741,642 A | 4/1998 | Rubin et al. | |
| 5,814,605 A * | 9/1998 | Pierce et al. | |
| 5,824,643 A | 10/1998 | Pierce et al. | |
| 5,830,879 A | 11/1998 | Isner | |
| 5,863,767 A | 1/1999 | Gospodarowicz et al. | |
| 5,965,530 A | 10/1999 | Pierce et al. | |
| 6,033,664 A | 3/2000 | Verheijen | |
| 6,174,855 B1 | 1/2001 | Hansson | |
| 6,187,330 B1 | 2/2001 | Wang et al. | |
| 6,239,172 B1 | 5/2001 | Kaesemeyer | |
| 6,297,238 B1 | 10/2001 | Doyle et al. | |
| 6,319,522 B1 | 11/2001 | Ballard et al. | |

FOREIGN PATENT DOCUMENTS

| | | | |
|---|---|---|---|
| EP | 0 251 806 A2 | | 1/1988 |
| EP | 0 307 847 A2 | | 3/1989 |
| EP | 307847 | * | 3/1989 |
| EP | 0 357 240 A2 | | 3/1990 |
| EP | 0 619 370 A1 | | 10/1994 |
| EP | 619370 | * | 10/1994 |
| EP | 1 264 601 A2 | | 12/2002 |
| GB | 2 146 335 A | | 4/1985 |
| WO | WO 8203772 | * | 11/1982 |
| WO | WO 97/13857 | * | 4/1997 |
| WO | WO 98/16243 | * | 4/1998 |

OTHER PUBLICATIONS

Aaronson, Stuart A., et al., "Keratinocyte Growth Factor. A Fibroblast Growth Factor Family Member with Unusual Target Cell Specificity", Annals of the New York Academy of Sciences, 1991, vol. 638, pp. 62-77.

Bajaj-Elliott, Mona, et al., "Keratinocyte Growth Factor in Inflammatory Bowel Disease. Increased mRNA Transcripts in Ulcerative Colitis Compared with Crohn's Disease in Biopsies and Isolated Mucosal Myofibroblasts", American Journal of Pathology, Nov. 5, 1997, vol. 151 (No. 5), pp. 1469-1476.

Baskin, Laurence S., et al., "Growth Factors in Bladder Wound Healing", Journal of Urology, Jun. 1997, vol. 157, pp. 2388-2395.

Bechtel, Michael J., et al., "Upregulation of Cell-Surface-Associated Plasminogen Activation in Cultured Keratinocytes by Interleukin-1β and Tumor Necrosis Factor-α", Experimental Cell Research, 1996, vol. 223, pp. 395-404.

Beer, Hans-Dietmar, et al., "Mouse Fibroblast Growth Factor 10: cDNA Cloning, Protein Characterization and Regulation of mRNA Expression", Oncogene, 1997, vol. 15, pp. 2211-2218.

Bellosta, P., et al., "Cleavage of K-FGF Produces a Truncated Molecule with Increased Biological Activity and Receptor Binding Affinity", Journal of Cell Biology, 1993, vol. 121, pp. 705-713.

Bugge, Thomas H., et al., "Loss of Fibrinogen Rescues Mice from the Pleiotropic Effects of Plasminogen Deficiency", Cell, 1996, vol. 87, pp. 709-719.

Carmeliet, Peter, et al., "Genetic Analysis of Blood Vessel Formation Role of Endothelial Versus Smooth Muscle Cells", Trends in Cardiovascular Medicine, 1997, vol. 7, pp. 271-281.

Carmeliet, Peter, et al., "Inhibitory Role of Plasminogen Activator Inhibitor-1 in Arterial Wound Healing and Neointima Formation—A Gene Targeting and Gene Transfer Study in Mice". Circulation, 1997, vol. 96, pp. 3180-3191.

Carmeliet, Peter, et al., "Development and Disease in Proteinase-Deficient Mice: Role of the Plasminogen, Matrix Metalloproteinase and Coagulation System", Thrombosis Research, 1998, vol. 91, pp. 255-285.

Chedid, Marcio, et al., "Glucocorticoids Inhibit Keratinocyte Growth Factor Production in Primary Dermal Fibroblasts", Endocrinology, 1996, vol. 137, pp. 2232-2237.

Collen, Desire, et al., "Fibrinolysis and the Control of Hemostasis", The Molecular Basis of Blood Diseases, Ed. G. S. Stamatoyannopoulos, A. W. Nienhuis, P. W. Majerus, and H. Varmus. Philadelphia: W. B. Saunders Co., 1994, pp. 725-752.

Collen, Desire, "The Plasminogen (Fibrinolytic) System", Thrombosis and Haemostasis, 1999, vol. 82, pp. 259-270.

Farrell, Catherine L., et al., "Keratinocyte Growth Factor Protects Mice from Chemotherapy and Radiation-induced Gastrointestinal Injury and Mortality", Cancer Research, 1998, vol. 58, pp. 933-939.

(Continued)

Primary Examiner—Michael Meller
(74) Attorney, Agent, or Firm—Jackson Walker L.L.P.

(57) ABSTRACT

A composition combining an extracellular matrix-degrading protease and a growth factor related to epithelial cell functions together without inactivation or degradation of the growth factor by the protease. Preferably, the protease is plasmin/plasminogen or a related one, and the growth factor is KGF or a related one. The combination associates two independent, but synergistic functions essential to the re-epithelialization process or healing process, i.e, stimulating epithelial cell proliferation/differentiation and facilitating its migration by clearing the extracellular matrix components. The combination may be constructed in various ways and can be used to treat wounds or any other disease conditions involving cells of epithelial origin or any other cell types that the growth factor may affect.

5 Claims, 8 Drawing Sheets

OTHER PUBLICATIONS

Finch, Paul W., et al., "Human KGF Is FGF-Related with Properties Fehrenbach, H., et al., "Keratinocyte Growth Factor-induced HyperPlasia of Rat Alveolar Type II Cells *in Vivo* is Resolved by Differentiation into Type I Cells and by Apoptosis", European Respiratory Journal, 1999, vol. 14, pp. 534-544. of a Paracrine Effector of Epithelial Cell Growth", Science, 1989, vol. 245, pp. 752-755.

Folkman, Judah, "Seminars in Medicine of the Beth Israel Hospital, Boston, Clinical Applications of Research of Angiogenesis", New England Journal of Medicine, 1995, vol. 333, pp. 1757-1763.

Gillis, Paul, et al., Keratinocyte Growth Factor Induces Angiogenesis and Protects Endothelial Barrier Function, Journal of Cell Science, 1999, vol. 112, pp. 2049-2057.

Helisch, Armin, et al., Therapeutic Angiogenesis in Ischemic Heart Disease, Thrombosis and Haemostasis, 1999, vol. 82, pp. 772-780.

Heymans, S., et al., "Inhibition of Plasminogen Activators or Matrix Metalloproteinases Prevents Cardiac Rupture but Impairs Therapeutic Angiogenesis and Causes Cardiac Failure", Nature Medicine, 1999, vol. 5, pp. 1135-1142.

Hiraoka, Nobuaki, et al., "Matrix Metalloproteinases Regulate Neovascularization by Acting as Pericellular Fibrinolysins", Cell, 1998, vol. 95, pp. 365-377.

Hoffman, Richard, et al., "Wound Fluid from Venous Leg Ulcers Degrades Plasminogen and Reduces Plasmin Generation by Keratinocytes", Journal of Investigative Dermatology, 1998, vol. 111, pp. 1140-1144.

Igarashi, Makoto, et al., "Characterization of Rcombinant Human Fibroblast Growth Factor (FGF)-10 Reveals Functional Similarities with Keratinocyte Growth Factor (FGF-7)", The Journal of Biological Chemistry, 1998, vol. 273, pp. 13230-13235.

Jimenez, Pablo A., et al., "Keratinocyte Growth Factor-2 Accelerates Wound Healing in Incisional Wounds", Journal of Surgical Research, 1999, vol. 81, pp. 238-242.

Johnson, Daniel E., et al., "Structural and Functional Diversity in the FGF Receptor Multigene Family", Advances in Cancer Research, 1993, vol. 60, pp. 1-41.

Kao, Winston W., et al., "Healing of Corneal Epithelial Defects in Plasminogen-and-Fibrinogen-Deficient Mice", Investigative Ophthalmology & Visual Science, 1998, vol. 39, pp. 502-508.

Komorowiez, Erzsebet, et al., "Fibrinolysis with Des-Kringle Derivatives of Plasmin and its Modulation by Plasma Protease Inhibitors", Biochemistry, 1998, vol. 37, pp. 9112-9118.

Lu, Weiqin, et al., "Fibroblast Growth Factor-10. A Second Candidate Stromal to Epithelial Cell Andromedin in Prostate", The Journal of Biological Chemistry, 1999, vol. 274, pp. 12827-12834.

Lund, Leif R., et al., "Functional Overlap between Two Classes of Matrix-degrading Proteases in Wound Healing", The European Molecular Biology Organization Journal, 1999, vol. 18, pp. 4645-4656.

Marchese, Cinzia, et al., "Modulation of Keratinocyte Growth Factor and its Receptor in Reepithelializing Human Skin", Journal of Experimental Medicine, 1995, vol. 182, pp. 1369-1376.

McKeehan, Wallace L., et al., "The Heparan Sulfate-Fibroblast Growth Factor Family: Diversity of Structure and Function", Progress in Nucleic Acid Research & Molecular Biology, 1998, vol. 59, pp. 135-176.

Morikoa, Shinji, et al., "Migrating Keratinocytes Express Urokinase-Type Plasminogen Activator", Journal of Investigative Dermatology, 1987, vol. 88, pp. 418-423.

Odekon, Lale E., et al., "Requirement for Receptor-Bound Urokinase in Plasmin-Dependent Cellular Conversion of Latent TGF-β to TGF-β", Journal of Cellular Physiology, 1994, vol. 158, pp. 398-407.

Osslund, Timothy D., et al., "Correlation Between the 1.6 Angstrom Crystal Structure and Mutational Analysis of Keratinocyte Growth Factor", Protein Science, 1998, vol. 7, pp. 1681-1690.

Romer, John, et al., "The Receptor for Urokinase-type Plasminogen Activator is Expressed by Keratinocytes at the Leading Edge During Re-Epithelialization of Mouse Skin Wounds", Journal of Investigative Dermatology, 1994, vol. 102, pp. 519-522.

Romer, John, et al., "Impaired Wound Healing in Mice with a Disrupted Plasminogen Gene", Nature Medicine, 1996, vol. 2, pp. 287-292.

Ron, Dina, et al., "Expression of Biologically Active Recombinant Keratinocyte Growth Factor. Structure/Function Analysis of Amino-Terminal Truncation Mutants", Journal of Biological Chemistry, 1993, vol. 268, pp. 2984-2986.

Rubin, Jeffrey S., et al., "Purification and Characterization of a Newly Identified Growth Factor Specific for Epithelial Cells", Proceedings of the National Academy of Sciences of the United States of America, 1989, vol. 86, pp. 802-806.

Salva, Ushma, et al., "Barrier Function of Airway Epithelium: Effects of Radiation and Protection by Keratinocyte Growth Factor", Radiation Research, 1998, vol. 150, pp. 195-203.

Schlessinger, Joseph, et al., Regulation of Growth Factor Activation by Proteoglycans: What is the Role of the Low Affinity Receptors?, Cell, Nov. 3, 1995, vol. 83, pp. 357-360.

Staiano-Coico, Lisa, et al., Human Keratinocyte Growth Factor Effects in a Porcine Model of Epidermal Wound Healing, Journal of Experimental Medicine, 1993, vol. 178, pp. 865-878.

Tagashira, Shuzo, et al., "Cloning of Mouse FGF10 and Up-Regulation of Its Gene Expression During Wound Healing", Gene, 1997, vol. 197, pp. 399-404.

Tsuboi, Ryoji, et al., "Keratinocyte Growth Factor (FGF-7) Stimulates Migration and Plasminogen Activator Activity of Normal Human Keratinocytes", Journal of Investigative Dermatology, 1993, vol. 101, pp. 49-53.

Van Setten, Gysbert-Botho, et al., "Plasmin and Plasminogen Activator Activities in Tear Fluid During Corneal Wound Healing after Anterior Keratectomy", Current Eye Research, 1989, vol. 8, pp. 1293-1298.

Weissman, Bernard E., et al., "BALB and Kirsten Murine Sarcoma Viruses alter Growth and Differentiation of EGF-Dependent BALB/c Mouse Epidermal Keratinocyte Lines", Cell, 1983, vol. 32, pp. 599-606.

Werner, Sabine, et al., "Large Induction of Keratinocyte Growth Factor Expression in the Dermis during Wound Healing", Proceedings of the National Academy of Sciences of the United States of America, 1992, vol. 89, pp. 6896-6900.

Werner, Sabine, et al. "The Function of KGF in Morphogenesis of Epithelium and Reepithelialization of Wounds", Science, 1994, vol. 266, pp. 819-822.

Werner, Sabine, "Keratinocyte Growth Factor: A Unique Player in Epithelial Repair Processes", Cytokine & Growth Factor Reviews, 1998, vol. 9, pp. 153-165.

Wu, Liancun, et al., "Keratinocyte Growth Factor Induces Granulation Tissue in Ischemic Dermal Wounds. Importance of Epithelial-Mesenchymal Cell Interactions", Archives of Surgery, 1996, vol. 131, pp. 660-666.

Yamasaki, Masahiro, et al., "Structure and Expression of the Rat mRNA Encoding a Novel Member of the Fibroblast Growth Factor Family", Journal of Biological Chemistry, 1996, vol. 271, pp. 15918-15921.

Zeeh, Jorg M., et al., Kertinocyte Growth Factor Ameliorates Mucosal Injury in an Experimental Model of Colitis in Rats, Gastroenterology, 1996, vol. 110, pp. 1077-1083.

Zheng, Jie, et al., "Keratinocyte Growth Factor Enhances Urokinase-Type Plasminogen Activator Activity in HPV16 DNA-Immortalized Human Uterine Exocervical Epithelial Cells", 1996, European Journal of Cell Biology, 1996, vol. 69, pp. 128-134.

Database Derwent AN 1991-20470. "Novel Cataplasm for skin diseases—comprises back-lining and ointment layer contg. lysozyme, prepd. by spreading ointment and sealing", JP 03130215 A (Hitachi Chem Co Ltd.) Jun. 4, 1991, abstract.

U.S. Patent and Trademark Office—International Search Report—Oct. 14, 2003.

Putnins EE, Firth JD, Uitto VJ. Keratinocyte growth factor stimulation of gelatinase (matrix metalloproteinase-9) and plasminogen activator in histiotypic epithelial cell culture. (Abstract). J Invest Dermatol. Jun. 1995;104(6):989-94.

Tsuboi R, Sato C, Kurita Y, Ron D, Rubin JS, Ogawa H. Keratinocyte growth factor (FGF-7) stimulates migration and plaminogen activator activity of normal human keratinocytes. (Abstract). J Invest Dermatol. Jul. 1993;101(1):49-53.

Werner S. Keratinocyte growth factor: a unique player in epithelial repair processes. Cytokine Growth Factor Rev. Jun. 1998;9(2):153-65.

Preliminary Notice of Rejection from the Taiwan Patent Office. Dated Apr. 26, 2006.

Preliminary Notice of Rejection from the Taiwan Patent Office (Translated to English). Dated Apr. 26, 2006.

Supplementary Partial European Search Report Under Rule 46(1) EPO, from the European Patent Office, dated Nov. 9, 2006.

* cited by examiner

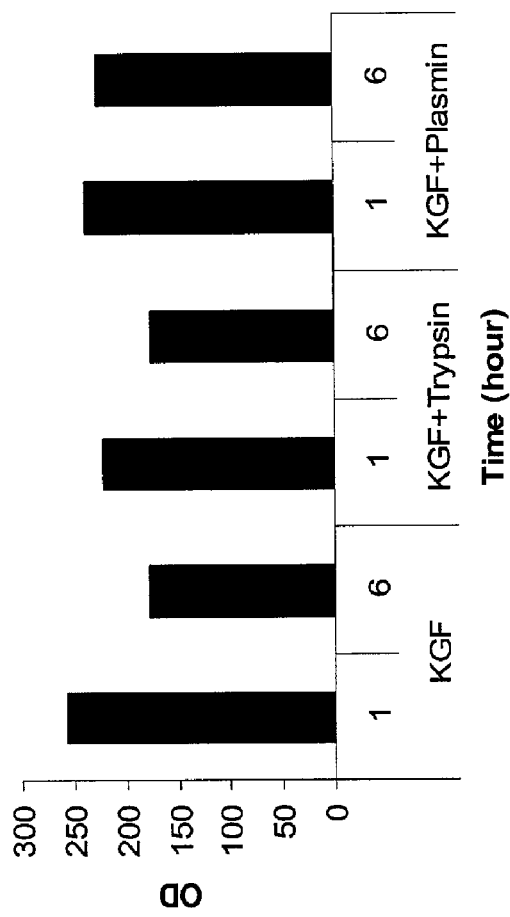
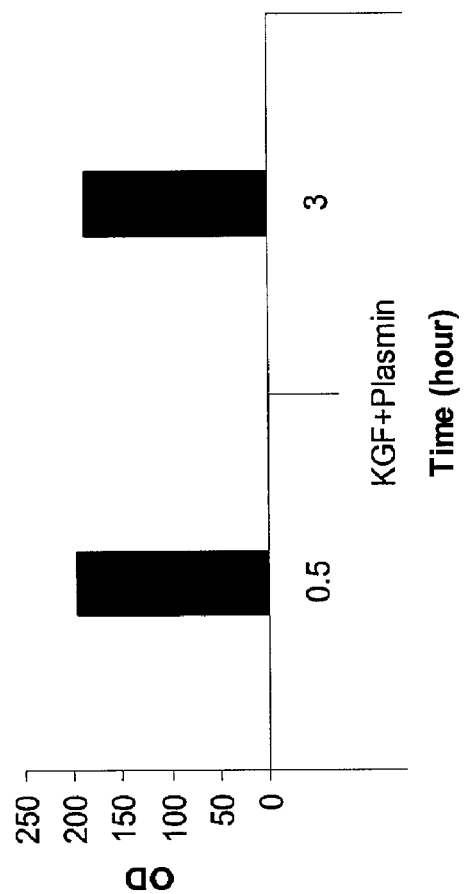
Fig. 4a
Fig. 4b

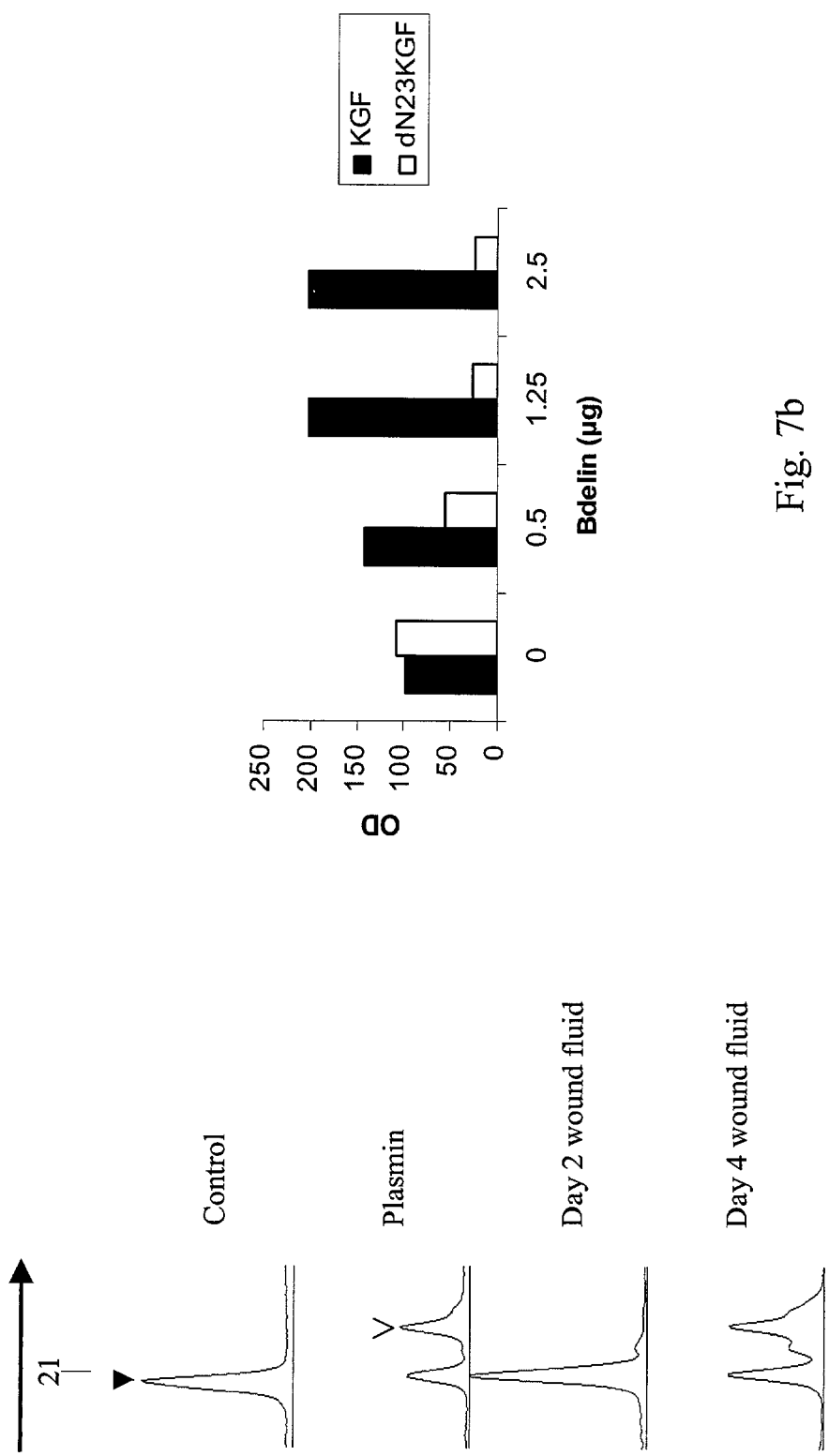

COMBINATION OF A GROWTH FACTOR AND A PROTEASE ENZYME

BACKGROUND

The present invention pertains to a composition comprising a combination formed by mixing two components: (1) a growth factor related to epithelial cell functions; and (2) an extracellular matrix-degrading protease for the purpose of enhancing healing of an injury in an animal, or human. The two components can be pre-combined before giving to the subject to be treated or given to the subject in a sequential manner. More specifically, this invention pertains to the combination of keratinocyte growth factors ("KGF") with plasmin, plasminogen, plasminogen activator, or its functional biological equivalent, which combination is used for the treatment of injuries involving cells of epithelial origin and other cell types that KGF may affect. In addition, the present invention pertains to a kit that holds a container with a growth factor and a container with an extracellular matrix-degrading protease enzyme. The contents of each container can either be in a carrier solution (e.g. water, buffer, saline, thickener, emulsion, or ointment), or lyophilized with the carrier solution in a third container for the user to reconstitute the components. A further goal of the present invention is to present a method for using the components of the kit for the purpose of enhancing wound healing. For example, the components of the kit are mixed and placed on an injury, or the individual components of the kit can be placed on the injury in a tandem or sequential order. Alternately, the components or biological equivalents of the kit can be purchased or fabricated and used with the described methods for the purpose of enhanced wound healing.

Epithelial cells account for one-third of all cells in the human body. Those in skin are referred to as keratinocytes. Epithelial cells are also found as the surface lining in the mouth, nasal tract, gastrointestinal tract, vaginal tract, and several other organs or tissues such as lung and cornea. Injuries or wounds involving epithelial cells occur in many different forms, including cuts, burns, and ulcers. They may be acute or chronic. Examples include pressure ulcers, venous stasis ulcers, diabetic foot ulcers, duodenal ulcers, ulcerative colitis, aphthous ulcers, cornea ulcers. The non-healing and slow-healing wounds are referred as chronic wounds. Chronic wounds in the form of oral or intestinal mucositis occur frequently in cancer patients receiving chemotherapy. They are a major health concern and are increasingly so because of the aging population.

Endothelial cells are another large population of cells in the human body. They make up the surface lining of all blood vessels. The vasculature of a 70 kg adult is lined by ~1,000 $m^2$ of endothelial cells. In the aging human population, vascular damage related to heart disease, stroke, and lower extremity ischemia is one of the most significant medical concerns. Heart disease involving large blood vessels can be treated with certain surgical procedures such as angioplasty or by-pass surgery. However, no effective treatment is available for disease conditions involving small blood vessels. Recently, a promising new treatment for these vascular disease conditions, i.e., therapeutic angiogenesis, is being developed, which involves delivery of an angiogenic growth factor that promotes new blood vessel formation. A therapeutic mixture comprised of L-arginine and angiogenic growth factors is disclosed in U.S. Pat. No. 6,239,172 for the treatment of diseases related to endothelial dysfunction, the entire content of which is hereby incorporated by reference.

Extracellular matrix is a vital fibrous matrix providing support and anchorage for cells in establishing the tissue structure and integrity and maintaining their normal functions. Its components include collagen, fibronectin, laminin, heparin sulfate proteoglycan, hyaluronic acid, and elastin. In the case of wounds, blood clots formed by fibrin fibers in or on the damaged tissues constitute another matrix component. For cells to migrate through this matrix during wound healing or normal tissue growth, the matrix degradation surrounding the migrating cells is required. Although not wanting to be bound by theory, many enzymes are known to participate in this degradation process, including collagenases, metalloproteases, and plasmin. An intricate system exists to regulate the activities of these enzymes. Many of them are produced by cells as an inactive proenzyme requiring activation, e.g., by another enzyme, before they can be functional. Some of these enzymes have receptors on cell surfaces, thus limiting their activities near the cells.

KGF is a member of the fibroblast growth factor ("FGF") family and is also known as fibroblast growth factor-7 ("FGF-7") (Werner, *Cytokine & Growth Factor Reviews* 9:153–165, 1998). Members of this family are characterized by their ability to bind heparin, which plays a critical role in mediating the interaction between growth factors and their receptors (Schlessiger et al., *Cell* 83:357–360, 1995). The prototypes of the FGF family, aFGF (FGF-1) and bFGF (FGF-2), have been widely studied. KGF was first isolated in 1989. (Rubin et al., *Proc. Natl. Acad. Sci. USA* 86:802–806 (1989)). Subsequently, the KGF gene was cloned and KGF was expressed in bacteria. Finch et al., *Science* 245, 752–755 (1989); Ron et al., *J. Biol. Chem.* 268:2984–2988 (1993); Rubin et al., U.S. Pat. No. 5,741,642. It is unique in that it is produced by cells of mesenchymal origin, but primarily acts on cells of epithelial origin. KGF stimulates the proliferation and differentiation of epithelial cells (Aaronson et al., *Annals of the New York Academy of Sciences* 638, 62–77, 1991).

Mature KGF is a 163-amino acid polypeptide. Structural and mutagenesis studies have shown that the heparin and receptor-binding domains are located near the center portion of the molecule. A KGF fragment consisting of residues 23–144 ($\Delta$23 KGF-R144Q) retains the original biological activity along with increased thermal stability. (Osslund et al., *Protein Science* 7:1681–1690 (1998)). U.S. Pat. No. 5,677,278 ("the '278 patent") discloses a truncated keratinocyte growth factor fragment ($\Delta$23 KGF or KGF lacking the first 23 amino acids from N-terminus) which exhibits at least a 2-fold increase in mitogenic activity as compared to a mature full-length keratinocyte growth factor. The '278 patent further relates to a conjugate of truncated KGF and a toxin molecule for use in treatment of hyperproliferative disease of the epidermis. Moreover, the '278 patent relates to a therapeutic composition containing truncated KGF and a pharmaceutically acceptable carrier and the use thereof for wound healing purposes. The entire content of the '278 patent is hereby incorporated by reference.

There are four types of FGF receptors ("FGFR"), FGFR1-FGFR4. Several isoforms of FGFRs have been identified. While aFGF binds to all four types of FGFRs, KGF is only known to bind to the IIIb isoform of FGFR2. KGF is highly expressed in skin wounds. Increased KGF expression has also been observed in the bladder and kidney following injury and in inflammatory bowel disease. Unlike other growth factors, KGF is persistently expressed at a high level during the course of healing (Werner et al., *Proc. Natl. Acad. Sci. USA* 89, 6896–6900, 1992). Animal studies have shown that applying KGF topically to a wound accelerates the healing. (Staiano-Coico et al., *J. Exp. Med.* 178:865–878 (1993); Pierce et al., *J. Exp. Med.* 179: 831–840 (1994); Wu et al., *Arch. Surg.* 131:660–666 (1996)). Systemic administration of KGF has been shown to reduce injury in experimentally induced colitis. KGF also protects epithelial cells in animals subjected to radiation and/or chemotherapy. Furthermore, glucocorticoid treatment, which is known to delay wound healing, suppresses KGF expression. The use of compositions and devices for the controlled release delivery of peptides and growth factors have been disclosed in U.S. Pat. No. 6,187,330 ("the '330 patent"). The '330 patent invention may be employed for local delivery of angiogenic basic fibroblast growth factor or vascular endothelial growth factor, and the entire content is hereby incorporated by reference.

In U.S. Pat. No. 5,965,530 ("the '530 patent") KGF was shown to act on other types of cells, and the entire content is hereby incorporated by reference. Based on extensive in vivo studies in animals, it has now been discovered that KGF stimulates proliferation, growth and differentiation of various types of cells, besides keratinocytes. This better understanding of the biological effects of KGF in vivo enables a wider use of this polypeptide as a therapeutic agent, suitably formulated in a pharmaceutical composition, for the specific treatment of disease states and medical conditions afflicting or affecting tissues and organs such as the dermal adnexae, the liver, the lung, and the gastrointestinal tract. Besides cells of epithelial origin, KGF has recently been shown to act on microvascular endothelial cells, but not those from large vessels such as the aorta. It stimulates chemotaxis and proliferation of microvascular endothelial cells and induces angiogenesis in the rat cornea. Gillis et al., *Journal of Cell Science* 112:2049–2057 (1999).

A growth factor similar to KGF has recently been identified, named FGF-10 or KGF-2 (Yamasaki et al., *Journal of Biological Chemistry* 271:15918–19521 (1996); Beer et al., *Oncogene.* 15:2211–2218 (1997); Igarashi et al., *Journal of Biological Chemistry.* 273:13230–13235 (1998); Jimenez and Rampy, *Journal of Surgical Research.* 81:238–242 (1999)). It is in the same FGF family and shares a 54% amino acid identity with KGF. It also acts primarily on epithelial cells. However, unlike KGF, FGF-10 also binds FGFR1 and binds more strongly to heparin. FGF-10 does not appear to be as highly expressed as KGF in skin wounds, although topical application of FGF-10 has been found to enhance the healing process.

Besides KGF and FGF-10, there are other growth factors that can stimulate epithelial cells. These growth factors include epidermal growth factor ("EGF"), hepatocyte growth factor ("HGF"), transforming growth factor-α ("TGF-α"), insulin-like growth factor I ("IGF-I"), and acidic fibroblast growth factor ("aFGF"). However, these growth factors also act on other types of cells such as fibroblasts, hepatocytes, and muscle cells.

The migration of epithelial cells, like that of many other cells, is thought to be closely associated with the expression of urokinase plasminogen activator ("uPA") and its receptor ("uPAR") (Morioka et al., *J. Invest. Dermatol.* 88:418–423, 1987; Romer et al., *J. Invest. Dermatol.* 102:519–522, 1994). The role of uPAR is to focus the uPA-mediated fibrinolysis or proteolysis on the cell surface. The uPAR binds the single-chain inactive uPA or scuPA, which is then converted to the active two-chain uPA. KGF has been shown to increase the expression of uPA in epithelial cells (Tsuboi et al., *J. Invest. Dermatol.* 101:49–53, 1993; Zheng et al., *European Journal of Cell Biology* 69:128–134, 1996). uPA converts plasminogen to plasmin. Plasminogen is a ~90 kDa glycoprotein and consists of five kringle domains and a protease domain. Activation occurs by cleavage of plasminogen at a single peptide bond (Arg 561-Val 562). The two chains remain linked together by a disulfide bond following activation. Plasminogen also binds to cell surfaces via plasminogen binding sites, which is then readily activated by uPAR-bound uPA. Tissue plasminogen activator (tPA) also activates plasminogen, but does not have a cell surface receptor and requires binding to fibrin for optimal enzyme activity. Plasminogens lacking the first four or all five kringle domains are referred to as mini-plasminogen or micro-plasminogen. They can be similarly activated as plasminogen. Komorowicz et al., *Biochemistry* 37:9112–9118 (1998).

Plasmin/plasminogen is the key enzyme in fibrinolysis (Collen, *Thrombosis and Haemostasis* 82:259–270, 1999). It is responsible for degrading fibrin clots and other extracellular matrix components, but it is also involved in activation of metalloproteases and growth factors such as TGF-β. Besides uPA and tPA, plasminogen can also be activated by other enzymes, including streptokinase, staphylokinase, and common vampire bat plasminogen activator. Recent studies have shown that plasmin is critical for wound healing. Mice with a plasminogen gene knock-out exhibited delayed skin wound healing as the result of excess fibrin deposition, which in turn prevents keratinocyte migration (Romer et al., *Nature Medicine* 2: 287–292, 1996). If the fibrinogen gene is also deleted in these mice, wound healing ability is rescued (Bugge et al., *Cell* 87:709–19, 1996). The importance of plasmin has also been observed in the healing of artery and corneal injuries (Carmeliet et al., *Circulation* 96:3180–91 (1997); Kao et al., *Investigative Ophthalmology & Visual Science* 39:502–508 (1998)). In chronic venous leg ulcers, a defect in plasminogen has been observed (Hoffman et al., *J. Invest. Dermatol.* 111: 1140–4, 1998). Furthermore, deletion of uPA and/or tPA gene also causes delayed wound healing as a result of excess fibrin deposition. (Bugge et al., *Proc. Natl. Acad. Sci. USA* 93:5899–5904 (1996); Heymans et al., *Nature Medicine.* 5:1135–1142 (1999)). The plasmin has been used as a topical agent for treatment of wounds and has also been evaluated as an injectable for treatment of thrombosis.

The initial step of angiogenesis includes the migration of endothelial cells, and also involves proteolytic degradation of the extracellular matrix. The expression of uPA and uPAR is upregulated in the migrating endothelial cells (Carmeliet and Collen, *Trends in Cardiovascular Medicine* 7:271–281, 1997). Although not wanting to be bound by theory, the plasminogen activators and plasminogen trigger a protease cascade that may play an important role in angiogenesis. Studies using gene knock-out mice have shown that uPA-deficient mice exhibited an impaired revascularization, even after the treatment with vascular endothelial growth factor (VEGF), a known angiogenic growth factor (Heymans et al., *Nature Medicine.* 5:1135–1142, 1999).

Besides plasmin/plasminogen, there are other enzymes that may be involved in fibrin degradation. One such class of enzyme is metalloprotease (MMP), which has over 20 members. MMP-12 and -14 are known to degrade fibrin. The healing of wounds on plasminogen-deficient mice was severely delayed, but the wounds eventually healed. In contrast, if a broad-spectrum MMP inhibitor (e.g. galardin) was applied to these mice, the healing of wounds was completely stopped (Lund et al., *EMBO J.*, 18, 4645–4656, 1999). The degradation of fibrin by MMP-14 also is involved in endothelial cell migration (Hiraoka et al., *Cell,* 95, 365–377, 1998).

The use of both thrombin inhibitors and recombinant plasminogen activators have been used in products to control the wound healing processes. For example, U.S. Pat. No. 6,174,855 disclose the use of a thrombin inhibitor in the manufacture of a product for use in the control of wound healing processes within the body, in particular, the inhibition or prevention of fibrin-related adhesion and/or scar tissue formation, as well as products for use in the control of wound healing processes within the body comprising polysaccharides (e.g., chitosans) and low molecular weight peptide-based thrombin inhibitors, and the entire content of which is hereby incorporated by reference. Additionally, U.S. Pat. No. 6,033,664 ("the '664 patent") discloses the use of non-bacterial plasminogen activators in the manufacture of a topical medical preparation for the treatment of slow- or non-healing wounds. In addition, the '664 patent relates to a composition comprising a physiologically acceptable carrier and an effective amount of a non-bacterial plasminogen activator, with the exclusion of tPA, and the entire content of which is hereby incorporated by reference.

Despite all advances, there is still a great need for agents that can effectively treat injuries involving cells of epithelial origin. As previously stated, prior art teaches that injuries can be treated with various mixtures of protein-derived growth factors or protein growth factors. Additionally, prior art teaches that a slow healing injury can be treated with proteolytic enzymes. The combined use of protein growth factors and proteolytic enzymes to aid in wound healing are counter-intuitive, even though the functions of the protein growth factors and the enzyme may seem to be complimentary. The most obvious reason for such reasoning is that proteolytic enzymes function to hydrolyze (digest) proteins. Thus, the combination of protein growth factors (e.g. KGF), and enzymes that digest proteins (e.g. plasminogen) would initially seem counter-productive as a treatment for wound healing to one with ordinary skill in the art. However, insight is provided in the present invention that suggests a synergistic effect by the combination of growth factors and proteolytic enzymes. It is particularly desired that such combinatorial agents are produced and used based on their intricate interaction under in vivo conditions.

SUMMARY

One embodiment of the present invention pertains to a composition comprising a combination formed by mixing two components: (1) a growth factor related to epithelial cell functions; and (2) an extracellular matrix-degrading protease, for the purpose of enhancing wound healing in an injury of a subject, such as an animal including humans. The two components can be "pre-mixed" before given to the subject, or the two components can be given sequentially to the subject. More specifically, the present invention relates to utilizing acidic fibroblast growth factor (fibroblast growth factor-1), keratinocyte growth factor (fibroblast factor-7), keratinocyte growth factor-2 (fibroblast factor-10), epidermal growth factor, transforming growth factor-α, transforming growth factor-β, insulin-like growth factor, hepatocyte growth factor, or functional biological equivalent of any of these growth factors in combination with plasmin/plasminogen, miniplasmin/miniplasminogen, microplasmin/microplasminogen, urokinase plasminogen activator, tissue plasminogen activator, streptokinase or a functional biological equivalent of these activators and/or proteases for the purpose of enhancing healing of an injury in an animal or human.

Another embodiment of the present invention pertains to a kit that holds a container with a growth factor and a container with an extracellular matrix-degrading protease enzyme. The contents of each container can either be in a carrier solution (e.g. water, buffer, saline, thickener, emulsion, or ointment), or lyophilized with the carrier solution in a third container for the user to reconstitute the components. The components of the kit are mixed and placed on an injury of an animal or human for the purpose of enhancing wound healing. Alternately, the individual components of the kit can be placed on the injury in a tandem or sequential order.

A further embodiment of the present invention relates to a method of treating an injury in an animal or human by exploiting a combination of growth factors related to epithelial cell functions and extracellular matrix-degrading proteases. The method involves the utilization of the kits described herein or their individual components. For example, the components of the kit are mixed and placed on an injury, or the individual components of the kit can be placed on the injury in a tandem or sequential order. Alternately, the components or biological equivalents of the kit can be purchased or fabricated and used with the described methods for the purpose of enhanced wound healing.

3a) KGF with plasmin;
3b) KGF with trypsin;
3c) FGF-10 with plasmin; and
3d) FGF-10 with trypsin.

FIG. 4. Prolonged digestion of KGF with trypsin or plasmin. Electrophoresis and protein staining are the same as in FIG. 1.

4a) KGF (1.74 μM) was digested with trypsin (1380 nM) or plasmin (960 nM). A sample was removed at 1 hr or 6 hrs following incubation at 37° C. The OD measurements of KGF (the control without enzyme treatment) and its cleavage fragment (dN23KGF) following trypsin or plasmin treatment are shown; and 4b) KGF (1.74 μM) was digested with plasmin (2400 nM). A sample was removed at 30 min or 3 hrs following incubation at 37° C. The OD measurements of the cleavage fragment (dN23KGF) are shown.

Figure 5:
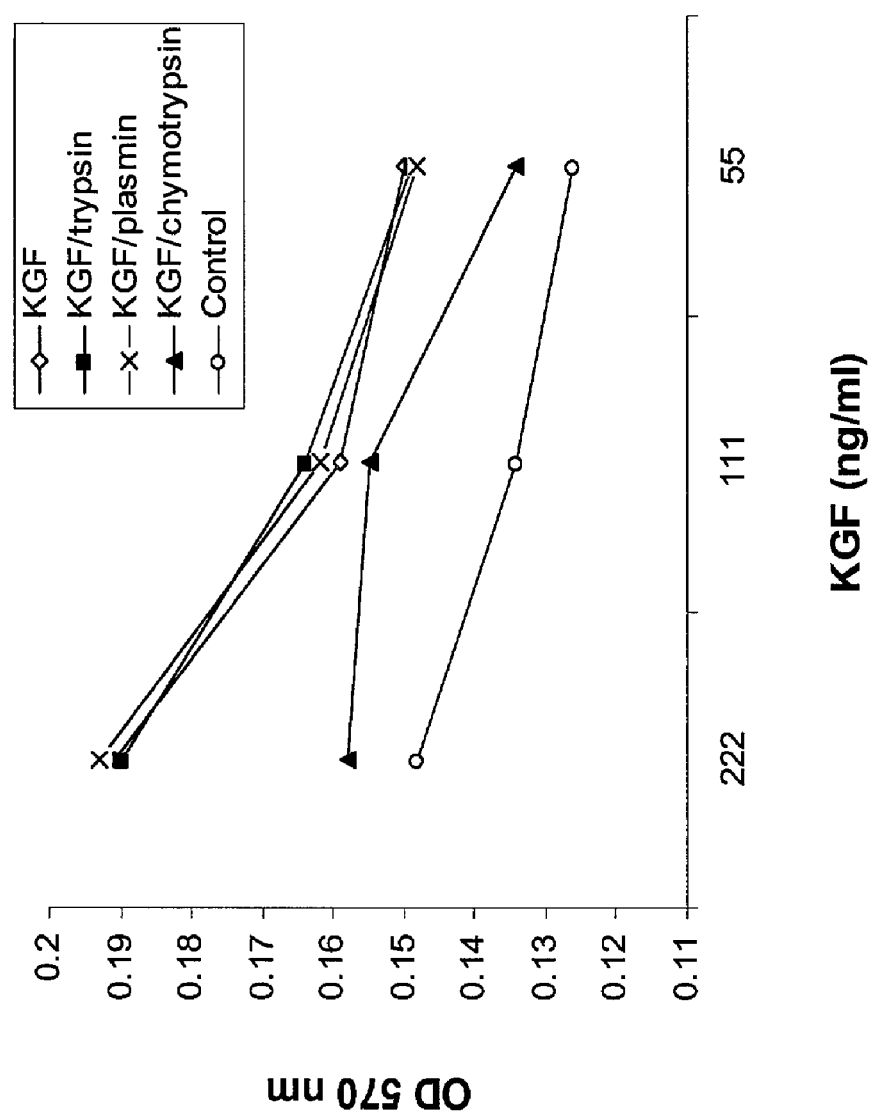

FIG. 5. Cell proliferation assay. KGF was treated with trypsin, plasmin, or chymotrypsin under the same conditions as in FIG. 1 except that the enzyme concentration was 2 times higher for each enzyme. The reaction mixtures were mixed with FBS and diluted in EMEM containing 0.5% FBS before being applied to the Balb/MK cells. After a 48-hr incubation at 37° C., the MTT dye was added. Cell lysis solution was added after an additional 4-hr incubation. Cells were kept in a wet chamber overnight before the OD at 570 nm was measured.

FIG. 6. Effect of KGF and plasminogen ("Plg") combination on keratinocyte migration and proliferation on fibrin gel and keratinocyte-mediated fibrinolysis.

6a) Cells were seeded onto the fibrin gel in a 24-well plate (1000 cells/well) and then treated with KGF, plasminogen, or their combination. After a five-day incubation at 37° C., cells that reached and adhered to the plate surface were counted using a hemocytometer following trypsin digestion; and 6b) Fibrin gel with or without plasminogen were formed over the Balb/MK cells (5000 cells/well) in a 24-well plate with or without KGF pre-treatment (37° C. for 3 hrs). After being incubated for 3 hrs at 37° C., the remaining fibrin gel along with media was removed from each well and centrifuged at 10,000 g for 5 min. The soluble protein concentration in the supernatant was determined by BCA assay.

FIG. 7. Cleavage of KGF by wound fluids. KGF was treated with wound fluids collected from full-thickness pig skin wounds at day 2 or day 4 post surgery in the presence or absence of bdelin. Proteins separated by gel electrophoresis and transferred to Immobilon-P membrane were probed with anti-KGF antibodies.

7a) Cleavage of KGF by wound fluids (5 µl) collected at day 2 or day 4 post surgery in a 10 µl reaction volume; and 7b) Inhibition of KGF cleavage by a day 4 wound fluid (5 µl) with Bdelin at various amounts in a 12.5 µl reaction volume. The molecular weight (kDa) of the standard is indicated on top. The electrophoresis direction is indicated by a solid arrow.

Figure 8:
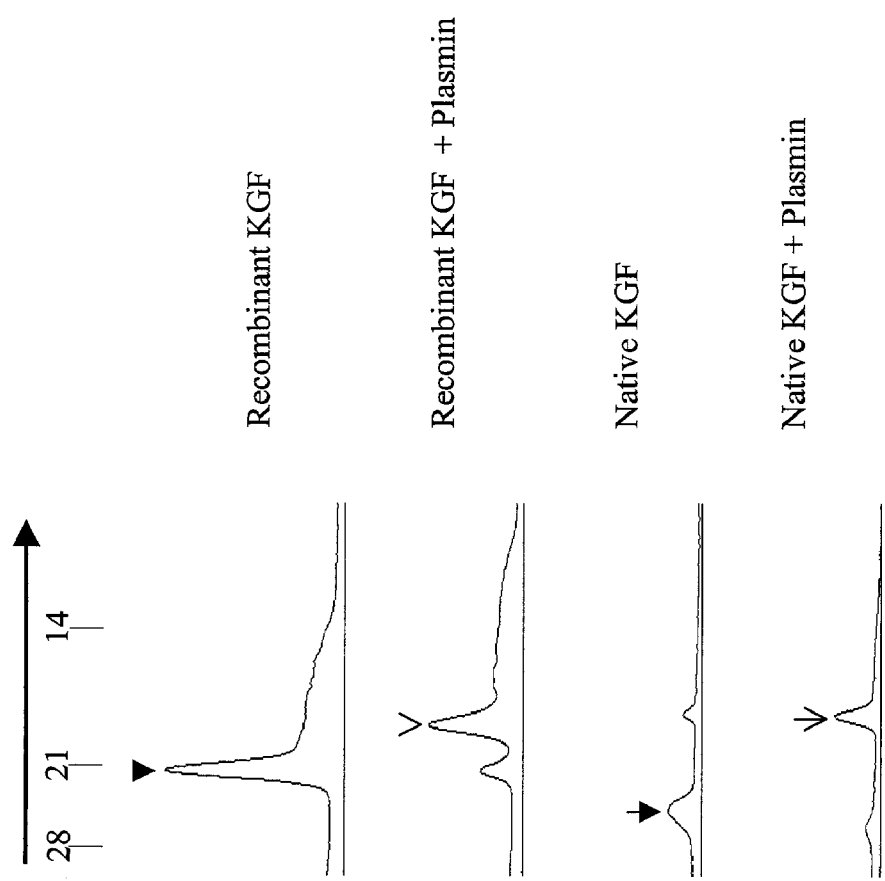

FIG. 8. Cleavage of native KGF by plasmin. Native KGF isolated from mouse fibroblast line 929 cells was treated with plasmin along with recombinant human KGF. Following treatment, proteins were separated by gel electrophoresis, transferred to Immobilon-P membrane, and probed with rabbit anti-KGF C-terminus antibody. Recombinant KGF and its cleavage fragment (dN23KGF; ~16 kDa) were indicated by closed and open arrow heads, respectively, whereas native KGF and its cleavage fragment (~16 kDa) were indicated by closed and open arrows, respectively. The molecular weight (kDa) of the standard is indicated on top. The electrophoresis direction is indicated by a solid arrow.

DETAILED DESCRIPTION OF PREFERRED EMBODIMENTS

Abbreviations:

The following abbreviations will be used herein: aFGF, acidic fibroblast growth factor; Arg, arginine; BCA, bicinchoninic acid; bFGF, basic fibroblast growth factor; CMC, carboxylmethyl cellulose; dN23KGF, the KGF molecule lacking the first 23 amino acids from N-terminus; EGF, epidermal growth factor; FGF, fibroblast growth factor; HGF, hepatocyte growth factor; IGF-I, insulin-like growth factor I; KGF, keratinocyte growth factor; Ser, serine; tPA, tissue plasminogen activator; transforming growth factor-α (TGF-α); transforming growth factor-β (TGF-β); uPA, urokinase plasminogen activator; uPAR, urokinase plasminogen activator receptor.

Terms:

The term "wound" refers to any disruption of the integrity of a tissue or organ, either external or internal. It is also used interchangeably with the term "injury". A wound may involve many different types of cells, including, epithelial, keratinocyte, fibroblast, hepatocyte, endothelial cells, and various immune cells such as macrophage. Injury that involves cells of epithelial origin include those in or on skin, muscosal surface, oral cavity, digestive track, eye, or lung.

The term "recombinant protein" refers to a protein or an active part of a protein produced in either prokaryotic or eukaryotic systems with the appropriate expression vectors carrying the DNA sequence coding for the protein. The DNA sequence coding for the protein can be either synthetic or cloned from the mRNA of cells using the molecular biology techniques well known in the arts.

The term "nucleic acid expression construct" refers to any type of genetic construct comprising a nucleic acid coding for RNA capable of being transcribed. The term "expression vector" can also be used interchangeably.

The term "functional biological equivalent" of growth factors, extracellular matrix degrading protease enzymes, or plasminogen activators, as used herein, is a polypeptide that naturally has, or has been, engineered to contain a distinct amino acid sequence while simultaneously having similar or improved biological activity when compared to the wild-type growth factor, enzyme, or enzyme activator.

The term "vector" refers to any vehicle that delivers a nucleic acid into a cell or organism. Examples include plasmid vectors, viral vectors, liposomes, or cationic lipids.

The term "cleavage" refers to a cut or separation of a molecule into two or more pieces with the possibility that at least one piece is a stable product that cannot be further cut, as detected with a given technique, and may retain all or most of the original activity associated with the molecule.

The term "degradation" refers to a cut or separation of molecules into small pieces that are undetectable with a given technique.

The term "a related enzyme" refers to an enzyme that is related to another by its function, specificity, structure, or being a part of the same enzyme cascade.

The term "a related growth factor" refers to a growth factor that is related to another by its function or structure.

The molecular biology techniques include those for isolation, purification, production, analysis, modification, and manipulation of nucleic acid and protein molecules. Recombinant DNA techniques refer to those used to isolate, purify, and manipulate DNA sequence. These techniques are well described in *Current Protocols of Molecular Biology* (Ausubel et al., eds., vol. 1–4, John Wiley & Sons) and *Molecular Cloning* (Sambrook J et al., vol. 1–3, $2^{nd}$ ed., 1989, Cold Spring Harbor Press). Example of these techniques include isolation and purification of nucleic acid or proteins, reverse transcription, PCR (polymerase chain reaction), in-vitro mutagenesis, restriction enzyme cut, cloning into various (plasmid) vectors, transfection, transformation, and protein expression in prokarotic (bacteria) or eukarotic cells (yeast, insect, or mammalian).

Although prior art teaches that wounds or injuries can be treated with proteolytic enzymes or protein growth factors independently, the simultaneous use of both would initially seem counter-intuitive, even though the functions of the protein growth factors and the enzyme may seem to be complimentary. The most obvious reason for such reasoning is that proteolytic enzymes function to hydrolyze (digest) proteins. Thus, the combination of protein growth factors (e.g. KGF), and enzymes that digest proteins (e.g. plasmin) would initially seem counterproductive as a treatment for wound healing to one with ordinary skill in the art. However, insight is provided in the present invention that suggests a synergistic effect by combination of growth factors and proteolytic enzymes. It is particularly desired that such combinatorial agents are produced and used based on their intricate interaction under in vivo conditions.

It is discovered that human KGF can be cleaved by plasmin or trypsin at the Arg23-Ser24 bond from the N-terminus, and the resulting fragment dN23KGF (KGF lacking the first 23 amino acids from N-terminus) is stable against enzyme digestion. Only high enzyme concentrations result in a slight degradation of dN23KGF as noted with trypsin. Furthermore, uPA and tPA, which convert plasminogen to plasmin, have no effect on KGF. Equally important, the dN23KGF remains as active as the intact KGF. Removal of two additional amino acids by chymotrypsin produces the dN25KGF (KGF with deletion of the first N-terminal 25 amino acids) with a reduced biological activity. These results are consistent with previous analysis of the functional domains of KGF by recombinant DNA technique, i.e., the N-terminus of KGF can be removed up to amino acid 23 (arginine) without losing any biological activity (Ron et al., *J. Biol. Chem.* 268, 2984–2988 (1993); Osslund et al., *Protein Science* 7, 1681–1690 (1998)). Plasmin cleaves proteins at arginine or lysine residues, and because there are many potential plasmin cleavage sites on KGF based on its primary sequence (i.e. it has 10 arginine and 17 lysine residues), the cleavage at this particular site of Arg23 with generation of a stable active fragment (dN23KGF) is unexpected.

It is also found that KGF was cleaved by plasmin in wound fluids and the native KGF isolated from fibroblasts was also cleaved by plasmin, yielding a C-terminal fragment having an identical size as dN23KGF obtained with recombinant KGF. Furthermore, combination of plasminogen and KGF synergistically increased keratinocyte-mediated fibrin lysis and migration and proliferation of keratinocytes. Thus, although not wanting to be bound by theory, it appears that KGF and plasmin act on two independent, but synergistic aspects of epithelial cell functions during the wound healing or re-epithelialization process; KGF stimulates the proliferation of epithelial cells, whereas plasmin (or indirectly plasminogen activator) facilitates their migration by clearing the fibrin clot and related extracellular matrix components.

Although not wanting to be bound by theory, dN23KGF might have an enhanced biological activity that may not be revealed by the current in vitro assay system used and can be due to many factors including increased affinity to cellular receptors and/or protein structure stability. At the same time, the cleavage may also serve as the initial step of the whole growth factor degradation process. The '278 patent disclosed that increased mitogenic activity was observed with the Δ23KGF (KGF molecule lacking the first 23 amino acids from N-terminus) which is similar, if not identical, to the dN23KGF.

Plasminogen concentration in plasma is high (1.5-2 µM or 135–180 µg/ml) (Collen and Lijnen, Fibrinolysis and the Control of Hematostasis, in *The Molecular Basis of Blood Diseases* (G. S. Stamatoyannopoulos, A. W. Nienhuis, P. W. Majerus, and H. Varmus, eds). W. B. Saunders Co (1994), Pages 725 to 752). The plasmin concentration in a wound or wound fluid has not been extensively examined. It has been reported that the plasmin concentration in tear fluid during corneal wound healing is ~37.9 µg/ml (van Setten et al., *Current Eye Research* 8:1293–1298, 1989). Although not wanting to be bound by theory, the highest possible plasmin concentration is the actual plasminogen concentration in plasma assuming that no specific enrichment mechanism is involved. The plasmin concentration in wounds is likely influenced by the expression level of uPA and/or tPA and the wound condition. The highest plasmin concentration used in the present experiments is 2400 nM or 213 µg/ml, which is above the highest possible physiological concentration under in vivo conditions. At one-fifth of this concentration, plasmin completely cleaves KGF at 1.74 µM or 33 µg/ml. There is only a minimal (<5%) or no degradation of the cleavage fragment (dN23KGF) observed at all plasmin concentrations tested over an extended incubation period at 37° C.

Not all growth factor proteins are stable under degradation conditions. For example, FGF-10 is another member of the same FGF family and is also known as KGF-2 due to its similarity with KGF. Both KGF and FGF-10 primarily act on epithelial cells, but differ with respect to heparin-binding strength, receptor-binding specificity, and expression level in wounds. Our experiments showed that FGF-10 was degraded by plasmin and trypsin leaving no stable cleavage fragment. These results further underscore the uniqueness of KGF in relation to effect of proteases present in the wound environment.

Thus, a unique combination of KGF and plasmin/plasminogen can be made and used for the treatment of injuries involving epithelial cells. Such a combination cannot be achieved with FGF-10, at least not with plasmin (the active enzyme). Although not wanting to be bound by theory, this combination, when properly formulated in a pharmaceutical composition can associate two independent, but synergistic functions that are essential to the re-epithelialization process (i.e., stimulating epithelial cell proliferation/differentiation and facilitating their migration by clearing fibrin clot and related extracellular matrix components). Indeed, the combination demonstrated the synergistic stimulation on keratinocyte proliferation and migration in the in vitro assay systems. Additionally, when KGF is cleaved by plasmin in wound fluids it reinforces the physiological relevance and potential benefit of the KGF and plasmin/plasminogen combination. This notion can be further strengthened by the finding that native KGF isolated from fibroblasts was also cleaved by plasmin, yielding a C-terminal fragment having an identical size as dN23KGF obtained with recombinant KGF.

Thus, the preferred embodiment of the present discovery is the combination of an extracellular matrix-degrading protease and a growth factor related to epithelial cell functions for treating a wound or disease conditions involving cells of epithelial origin or any other cell types that the growth factor may affect. The combination is achieved by:
1) physically mixing the two together either before or during application;
2) applying one first followed by another; or
3) using an alternate treatment scheme (i.e., treating the disease condition with one for one treatment period followed by another in the next treatment period).

It is preferred that the growth factor is not inactivated by the extracellular matrix-degrading protease in the active form. Additionally, the growth factor is related to epithelial cell function, and preferably is KGF or a related one. Moreover, the protease is directly or indirectly related to extracellular matrix degradation and is preferably plasmin/ plasminogen or a related one. The combination is used to treat wounds or injuries involving epithelial cells and other cell types that the growth factor may affect. The growth factors and the enzymes can be produced as native proteins by isolation from human or animal blood, tissues or cultured cells or as recombinant proteins by recombinant DNA techniques in prokaryotic or eukaryotic systems.

As modifications and/or changes may be made in the structure of the polynucleotides and/or proteins according to the present invention, while obtaining molecules having similar or improved characteristics, such biologically functional equivalents are also encompassed within the present invention.

A. Modified Polynucleotides and Polypeptides

The biological functional equivalent may comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skills in the art may wish to introduce a restriction enzyme recognition sequence into a polynucleotide while not disturbing the ability of that polynucleotide to encode a protein.

In another example, a polynucleotide may be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges on the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in which selected amino acids (or codons) may be substituted.

B. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids without detracting from the general scope of the invention.

C. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins. Vita et al. (1998). A structural motif that appears to be evolutionarily conserved in certain toxins is small (30-40 amino acids), stable, and highly permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, and also increase resistance to proteolytic degradation. Six, seven, eleven, twelve, thirteen and fourteen membered ring structures are also disclosed.

Methods for generating conformationally restricted beta turns and beta bulges are described, for example, in U.S. Pat. Nos. 5,440,013; 5,618,914; and 5,670,155. Beta-turns permit changing side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

Additionally, the preferred embodiment of the present discovery can be made in various techniques as outlined in Example 10. It is conceivable that such a combination may be made with many alternative enzymes or growth factors. Examples of alternative enzymes directly or indirectly related to extracellular matrix degrdation include uPA, tPA, streptokinase, staphylokinase, common vampire bat plasminogen activator, trypsin, collagenase, elastase, and metalloproteases. Enzymes that share the same specificity with plasmin may also be used. Examples of alternative growth factors related to epithelial cell functions include EGF, FGF-10, TGF-α, TGF-β, IGF-I, HGF, and aFGF. In particular, it is conceivable that FGF-10 may be combined with plasminogen (the inactive proenzyme) or a related enzyme.

In light of recent findings showing that KGF also stimulates other cell types, including microvascular endothelial cells and hepatocytes, the above-described combinations may also be used to treat disease conditions involving these cells. Plasminogen and plasminogen activators are also known to be involved in angiogenesis by facilitating the migration of endothelial cells. It is conceivable that KGF may be replaced with a different growth factor in combination when treating different cell types as long as the growth factor is not inactivated or degraded by the matrix-degrading protease.

EXAMPLE 1

Cleavage of KGF by Trypsin, Plasmin, and Chymotrypsin.

Several proteases were used to treat recombinant human KGF (163 amino acids) which was obtained from Promega (Madison, Wis.) or PeproTech (Rocky Hill, N.J.). Trypsin (13,000 units/mg protein), chymotrypsin (60 units/mg protein), and plasmin from porcine (3.2 units/mg protein) or human blood (5.7 units/mg protein) were obtained from Sigma Chemical Co. Two-chain urokinase plasminogen activator (uPA) from human urine (100,000 units/mg protein) and human tissue plasminogen activator (tPA) were obtained from Calbiochem (San Diego, Calif.). Both KGF and enyzmes were dissolved in TN buffer (25 mM Tris, 150 mM NaCl, pH 7.4). They were mixed at indicated concentrations and incubated in a water bath at 37° C. for 1 hr or more before mixed with equal volume of sample buffer and subjected to electrophoresis in 15% SDS-polyacrylamide gels under denaturing conditions. Electrophoresis was stopped when the dye (bromophenol blue) front migrated near to the end of the gel. The protein bands were visualized by Coomassie blue staining. Stained gel images were acquired using a GS-5000 digital imaging system with a CCD camera (Alpha Infotech Co.) under the settings allowing for acquisition at the full gray scale. The densitometry analysis of the protein bands was performed on a Macintosh computer using the public domain NIH Image 1.62 program (developed at the US National Institute of Health). Uncalibrated optical density (OD) of each band was measured. Comparison was only made between or among the bands on the same gel.

Figure 1:
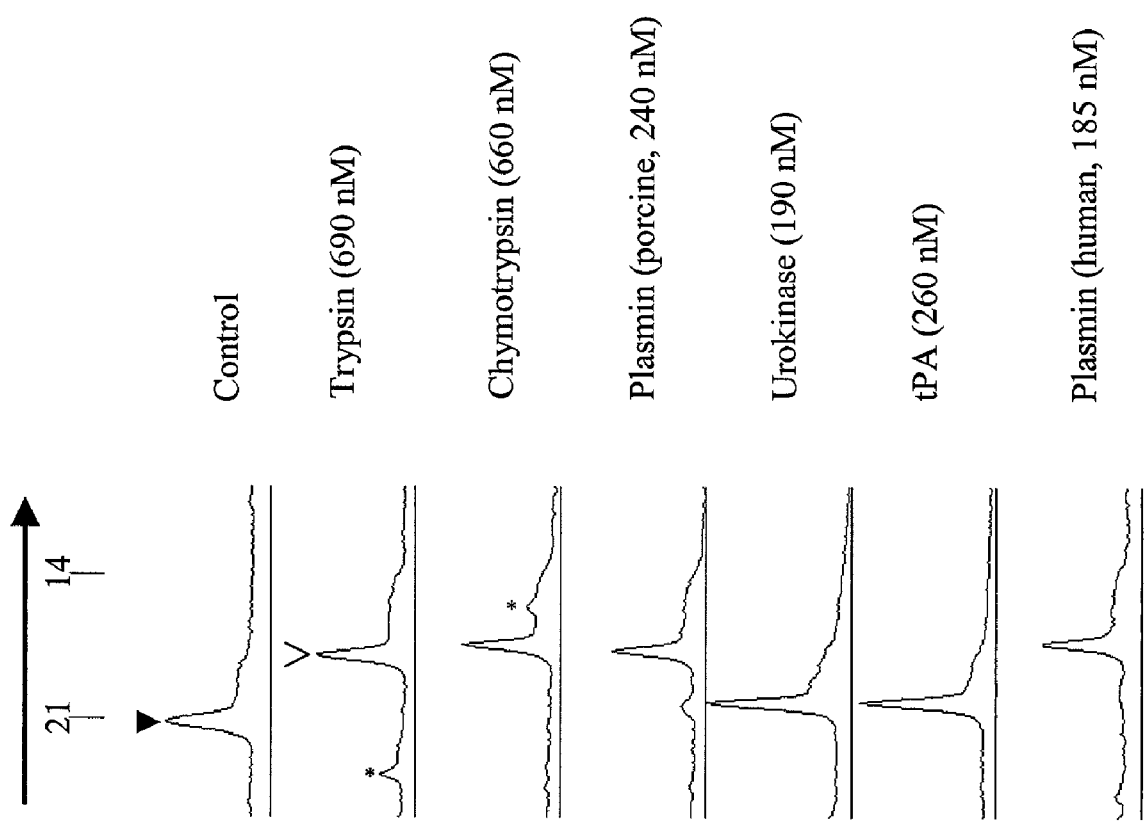
FIG. 1. Treatment of KGF with various proteases. KGF (1.74 μM) was treated with various proteases at indicated concentrations at 37° C. for 1 hr and then subjected to gel electrophoresis. Proteins were stained with Coomassie blue. The gel images were analyzed using NIH image 1.62. The scanning profiles of gel lanes are shown. KGF and its cleavage fragment (~16 kDa) were indicated by closed and open arrow heads, respectively. Protease band (s) within the molecular weight range shown are indicated with a star. The molecular weights (kDa) of standards are indicated on top. The electrophoresis direction is indicated by a solid arrow.

The results showed that trypsin, plasmin, and chymotrypsion cleaved KGF (1.74 µM) generating a fragment of ~16 kDa (FIG. 1). The fragment generated by trypsin and plasmin exhibited the same size, whereas the one generated by chymotrypsin appeared to be slightly smaller. tPA and uPA had no effect on KGF under the same conditions (FIG. 1). KGF remained intact when the concentrations of uPA and tPA were increased by 16 times to 3.04 µM and 4.16 µM, respectively. Plasminogen, the natural substrate for uPA and tPA, was used as a control for enzyme activity. uPA and tPA completely cleaved or activated 2.4 µM plasminogen at 1.2 nM and 0.1 µM, respectively. These results indicate that uPA and tPA do not have any effect on KGF.

EXAMPLE 2

Cleavage Sites on KGF.

Figure 2:
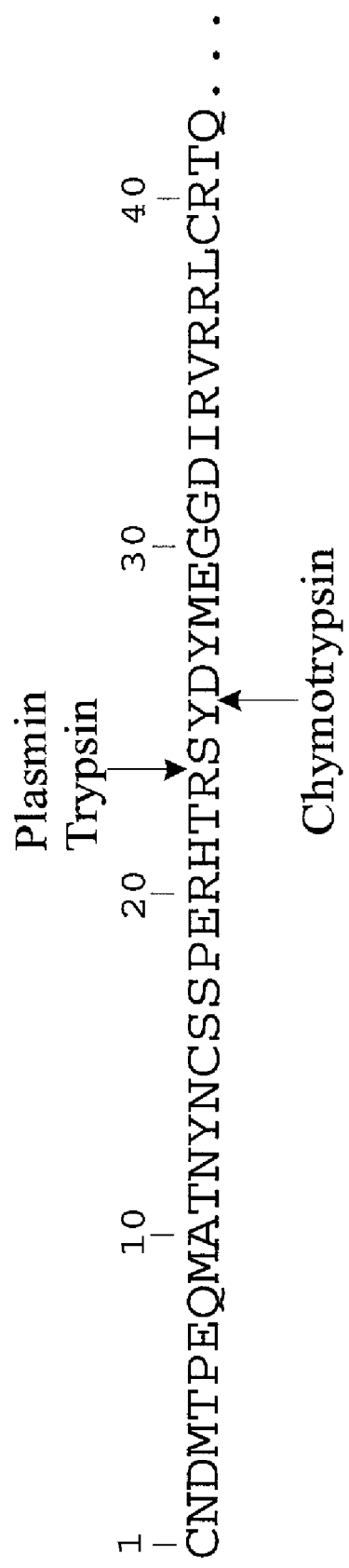
FIG. 2. The cleavage site of trypsin, plasmin, and chymotrypsin on KGF. The cleavage sites as identified by N-terminal sequencing of the ~16 kDa cleavage fragments (see Table 1) are indicated by arrows. The amino acids of mature KGF (163 amino acids) are sequentially numbered starting from the N-terminus.

The fragment generated by trypsin, plasmin, or chymotrypsin was subjected to N-terminal sequencing. KGF (2 µg) digested with trypsin, plasmin, or chymotrypsin was transferred to an Immobilon-P membrane (Millipore, Bedford, Mass.) following separation by gel electrophoresis. Proteins were stained by 0.1% Coomassie blue in 40% methanol and 10% acetic acid for ~20 sec and then de-stained with 40% methanol. The membrane was then washed with de-ionized water and air-dried. The ~16 kDa fragments generated by the enzymes were cut out for N-terminal amino acid sequencing using the Edman sequencing method on a Hewlett-Packard G1000A automated protein sequencer. The sequencing results allowed for identification of the cleavage sites. Thus, all enzymes cleaved KGF at the N-terminus, trypsin and plasmin at the Arg23-Ser24 and chymotrypsin at the Tyr25-Asp26 (Table 1, FIG. 2). Thus, trypsin and plasmin generated the dN23KGF (KGF with deletion of the first 23 amino acids from N-terminus) and chymotrypsin the dN25KGF (KGF with deletion of the first 25 amino acids from N-terminus).

A rabbit anti-KGF C-terminal peptide (CGKKTKKEQK-TAHFLPMAIT) antibody was generated using the synthetic peptide conjugated to KLH (Sigma-Genosys, Woundlands, Tex.). KGF, with or without plasmin treatment, was separated by electrophoresis and blotted onto Immobilon-P membrane. The membrane was probed with the anti-peptide antibody and the alkaline phosphatase-conjugated anti-rabbit IgG and the enzyme substrate BCIP/NBT (5-bromo-4-chloro-3-indolyl phosphate/nitro blue tetrazolium) were used for detection. The results showed that dN23KGF, like KGF, reacted strongly with this anti-peptide antibody, indicating that the C-terminus of the dN23KGF is intact or no cleavage involving more than 20 amino acids from the C-terminus has occurred. This is consistent with the size (~16 kDa) of dN23KGF; an additional deletion of 20 amino acids from the C-terminus would reduce the size of dN23KGF to ~14 kDa.

Thus, the dN23KGF is identical at the N-terminus to the Δ23KGF-144Q and Δ23KGF. It may also be identical at the C-terminus to the latter assuming no cleavage occurred at the C-terminus of dN23KGF as data have suggested. Both Δ23KGF-144Q and Δ23KGF have been shown to have the enhanced mitogenic effect or thermal stability or both.

EXAMPLE 3

Effect of Enzyme Concentration on the Stability of dN23KGF.

Figure 3C:
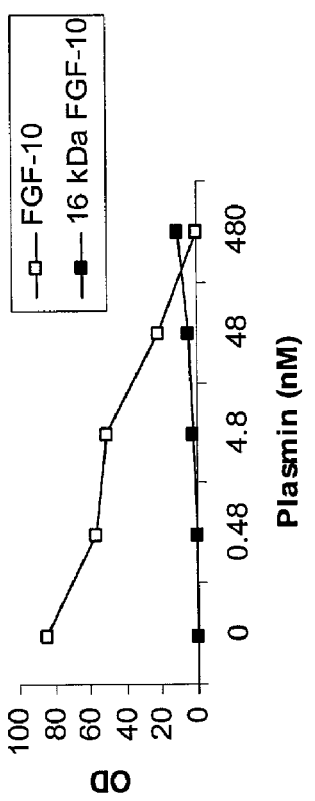
FIG. 3. Digestion of KGF and FGF-10 with trypsin or plasmin at various enzyme concentrations. KGF (1.74 μM) or FGF-10 (1.74 μM) was digested with trypsin or plasmin at various concentrations. Electrophoresis and protein staining are the same as in FIG. 1. The OD measurement of KGF and its cleavage fragment (dN23KGF) is shown along with that of FGF-10 and its cleavage fragment (~16 kDa).
Figure 3D:
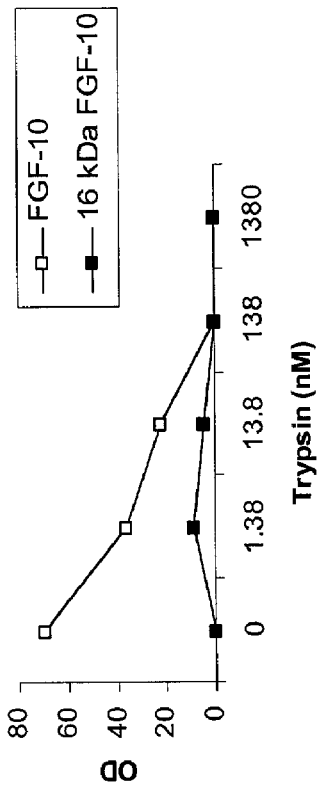
Figure 3A:
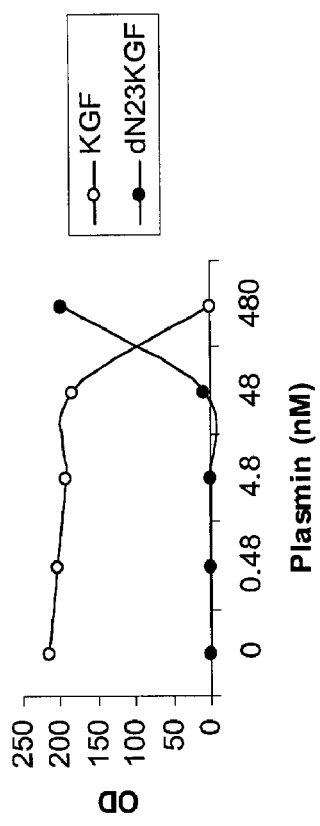
Figure 3B:
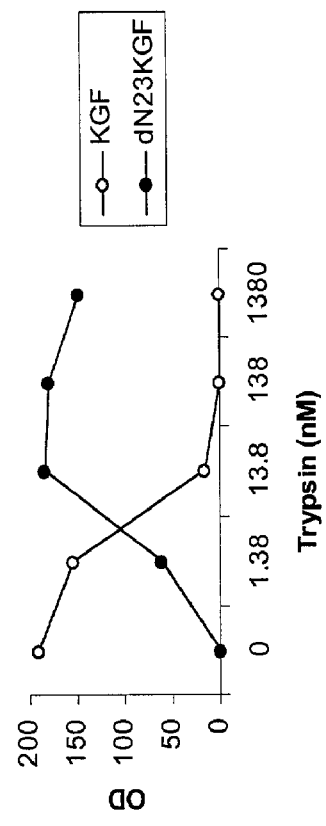

The enzyme digestion was performed at 37° C. for 1 hr as in Example 1, but at various enzyme concentrations. The results showed that the cleavage of KGF was enzyme concentration-dependent. A >50% cleavage of the intact KGF (1.74 µM) was achieved with trypsin at 13.8 nM or higher (FIG. 3b). In fact, nearly all KGF molecules were cleaved at 13.8 nM and a considerable cleavage was achieved at 1.38 nM. On the other hand, plasmin cleaved all KGF molecules at 480 nM, but only a small portion of them at 48 nM, which was less than that by trypsin at 1.38 nM (FIGS. 3a and 3b). The same result was obtained with either human or porcine plasmin. Thus, plasmin was less efficient than trypsin in cleaving KGF by ~34fold (FIGS. 3a and 3b).

It was observed that while KGF molecules were all or nearly all cleaved, the dN23KGF fragment generated by trypsin at the high enzyme concentration (1380 nM) was less than that at lower enzyme concentrations (138 nM and 13.8 nM) by 17% and 20%, respectively (FIG. 3b). This indicates that dN23KGF is further degraded to some extent at the high trypsin concentration (1380 nM). However, this observation also showed that increasing the trypsin concentration by 10 times from 13.8 to 138 nM did not significantly increase the degradation of dN23KGF fragment.

The removal of the first 23 amino acids from the N-terminus of KGF results in a 14% reduction in mass. Consistent with this calculation was the observation by densitometry measurement that dN23KGF accounted for ~90% of the original KGF with plasmin at all enzyme concentrations tested (480 and 960 nM) when a 100% cleavage was achieved (FIGS. 3a and 4). This indicates that dN23KGF is stable against plasmin at the concentrations used. Similarly, dN23KGF accounted for ~86% of the original KGF with trypsin at lower enzyme concentrations (138 and 13.8 nM), although it only accounted for ~71% at the high enzyme concentration (1380 nM) due to further degradation (FIG. 3b).

Although not wanting to be bound by theory, the role of plasmin in fibrinolysis is to degrade fibrin. As a control for enzyme activity, plasmin and trypsin were used to treat fibrinogen using the same conditions as for the KGF digestion. Plasmin degraded fibrinogen (490 nM) to smaller fragments completely at 48 nM or higher, although only minimally at 4.8 nM. Trypsin, like plasmin, can also cleave fibrin(ogen), generating similar cleavage products. Komorowicz et al., *Biochemistry* 37:9112–9118 (1998). Trypsin at 13.8 nM cleaved fibrinogen (490 nM) to a similar extent as the plasmin at a concentration between 4.8 and 48 nM. Thus, trypsin is at best only ~3 times more efficient than plasmin in degrading fibrinogen, as compared to the 34-fold higher efficiency with KGF. Thus, plasmin appears to be more efficient in cleaving fibrinogen than KGF.

EXAMPLE 4

Effect of Prolonged Enzyme Digestion on the Stability of dN23KGF.

To further evaluate the stability of dN23KGF exposed to trypsin or plasmin, the digestion at 37° C. was extended with samples taken at various times. The enzymes were used at a concentration higher than that needed to achieve a complete cleavage (FIGS. 3a and 3b). The results showed that compared to the amount of dN23KGF generated after a one-hour incubation, there was only a further 5% reduction with plasmin at 960 nM (86 µg/ml) following an additional 5 hrs of incubation (FIG. 4a). Furthermore, with the plasmin concentration increased to 2,400 nM (213 µg/ml), there was again only ~5% reduction observed when the amount of dN23KGF generated after a 30-minute incubation was compared to that after an additional 2.5 hrs of incubation (FIG. 4b).

With trypsin at 1380 nM (33 µg/ml), there was an 18% reduction in the amount of dN23KGF following an additional 5 hrs of incubation (FIG. 4a). Some of the observed reduction in the amount of dN23KGF with either trypsin or plasmin may be due to the non-enzyme-related factors such as adherence to the surfaces of test tubes and/or auto-degradation. Such loss during incubation was evident, especially when the total protein concentration in a reaction was low (e.g., the KGF control) and the incubation period was extended; a 27% reduction was noted with the KGF control after an additional 5 hrs of incubation (FIG. 4a). Under the same molar enzyme concentration, the total protein concentration (w/v) in a trypsin reaction would be ~3 fold lower than that in a plasmin reaction.

Together, these results, along with those described in Example 3, showed that dN23KGF was stable against plasmin digestion. It was also relatively stable against trypsin digestion, especially at lower enzyme concentrations.

EXAMPLE 5

Biological Activity of the dN23KGF.

Mouse keratinocyte line Balb/MK was used. Weissman and Aaronson, *Cell* 32:599–606 (1983). Cells were cultured in low-calcium medium EMEM (Biofluids, Washington, D.C.) with 10% FBS and 5 ng/ml epidermal growth factor (Promega, Madison, Wis.). For proliferation assays, cells were seeded into 96-well plate at $1-3 \times 10^3$ cells/well and incubated at 37° C. overnight. KGF was treated with the enzymes under the same conditions as in FIG. 1 except that the enzyme concentration was 2 times higher for each enzyme to ensure the complete cleavage of KGF which was verified by gel electrophoresis.

KGF or enzyme-treated KGF was first mixed with equal volume of FBS and then serially diluted in EMEM containing 0.5% FBS before being added to the cells (100 µl/well). After incubation at 37° C. for 48 hrs, an MTT (tetrazolium salt) proliferation assay was performed with a kit (CellTiter 96) from Promega (Madison, Wis.). Briefly, MTT dye was added to the wells (15 µl/well), and after 4 hrs at 37° C., the solubilization solution was added (100 µl/well). Plates were kept in a wet chamber overnight before the optical density (OD) at 570 nm was measured.

The results showed that the dN23KGF generated by trypsin or plasmin remained as active as the intact KGF. The fragment (dN25KGF) generated by chymotrypsin was less active than the intact KGF (FIG. 5). Enzymes alone had no effect on cell proliferation.

EXAMPLE 6

Effect of the Plasminogen and KGF Combination on Keratinocyte Migration and Proliferation and Keratinocyte-Mediated Fibrinolysis.

A keratinocyte migration assay on fibrin gel-coated surfaces was used to assess the effect of the plasminogen and KGF combination on keratinocyte migration and proliferation. Balb/MK cells were cultured as above. Human plasminogen-free fibrinogen (Calbiochem, San Diego, Calif.) in EMEM (3 mg/ml) was mixed with bovine thrombin at 0.02 unit/ml (Sigma Chemical Co, St. Louis, Mo.) and then placed into a 24-well plate (0.5 ml/well). Plates were kept at 37° C. for 3 hrs to allow the fibrin gel to form. Balb/MK cells were lifted from the flask with trypsin, washed three times with EMEM containing 10% FBS, suspended in EMEM containing 10% FBS (without EGF), and seeded onto the fibrin gel (1000 cells/well). After being incubated overnight, culture media were removed and replaced with EMEM containing plasminogen (0, 1, or 5 µg/ml), KGF (0 or 50 ng/ml), or both plasminogen and KGF. Cells were then cultured at 37° C.

Figure 6A:
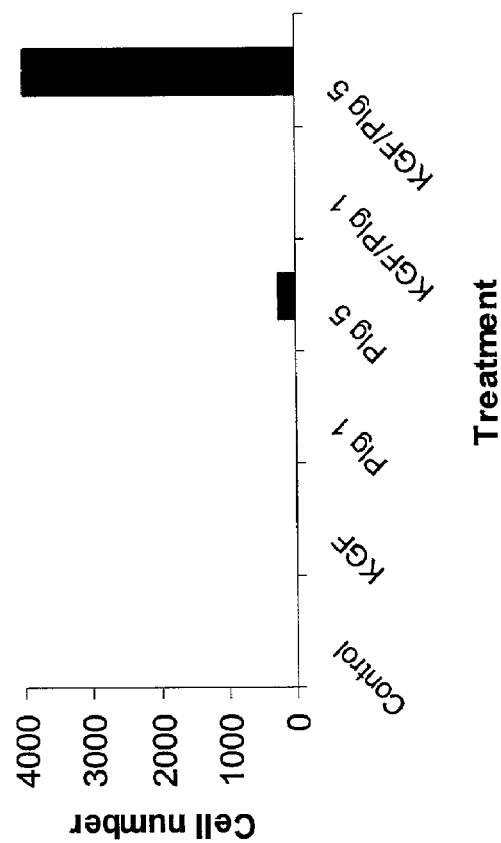

A clear digestion zone around individual cells on the fibrin gel was clearly visible after 24 hrs in the presence of plasmingen. Weak digestion zones was also noticed with the control (media alone) and KGF-treated cells after 48 hrs, and those around KGF-treated cells appeared to be more prominent compared to control cells. The appearance of clear digestion zones around individual cells indicated that fibrin lysis is a cell-mediated process; cells have plasminogen binding sites and express uPA that activates the plasminogen. By 48 hrs, cells treated with plasminogen at 5 µg/ml (with or without KGF) digested through the fibrin gel and adhered to plate surface. After being cultured for 5 days, still only those treated with plasminogen at 5 µg/ml completely digested through the gel. However, only those treated with the plasminogen (5 µg/ml) and KGF combination proliferated (FIG. 6a). These results indicated that for kertinocytes to migrate through fibrin gel and proliferate both KGF and plasminogen are required and KGF is functional in the presence of plasmin/plasminogen. The same results were obtained when plasminogen and/or KGF were first incorporated into the fibrin gel.

Figure 6B:
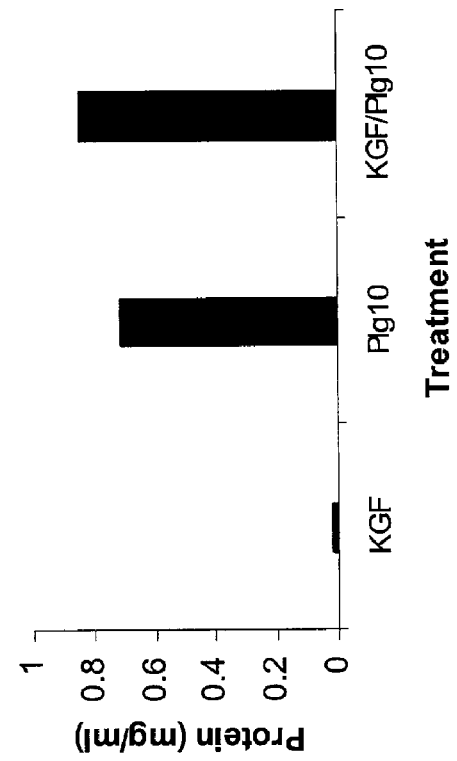

To further evaluate the effect of the plasmin/plasminogen and KGF combination on clearing the fibrin matrix, a fibrin digestion assay with keratinocytes was performed. This assay is based on the fact that the fibrin cleavage fragments generated by the plasmin digestion are soluble. Keratinocytes (Balb/MK) were seeded into a 24-well plate (5000 cells/well). Cells were cultured in EMEM with 10% FBS at 37° C. for 24 hrs and then in EMEM without FBS for another 24 hrs. A portion of the cells were first treated with KGF (50 ng/ml) for 3 hrs. Cells were then washed and received 0.5 ml of the fibrinogen solution in serum-free EMEM (5 mg/ml) with or without plasminogen (10 µg/ml). Thrombin was added to the fibrinogen solution (0.02 unit/ml) just before application. Cells were then cultured for another 3 hrs. The remaining fibrin gel, along with media, was removed from each well and centrifuged at 10,000 g for 5 min. The supernatant was removed and its protein content was determined by BCA assay. The serum-free EMEM was used as the background control. The results showed that only plasminogen induced a significant fibrin lysis (FIG. 6b). No fibrin lysis was observed with plasminogen-containing fibrin gel in empty wells. Pre-treatment of cells with KGF further increased the plasminogen-induced fibrin lysis by nearly 20% (FIG. 6b). Equally important, KGF and plasminogen combination treatment caused more cells to assume a migrating cell phenotype, i.e, they are fibroblast-like with long cytoplasma protrusions. These results showed that KGF and plasminogen synergistically enhanced fibrinolysis and facilitated the migration of keratinocyte. Although not wanting to be bound by theory, they most likely reflect the fact that KGF increases the uPA expression in keratinocytes and thus results in converting more plasminogen into plasmin, which in turn increases the fibrinolysis.

EXAMPLE 7

Degradation of FGF-10 by Various Enzymes.

FGF-10, also known as KGF-2, is a FGF similar to KGF. Thus, FGF-10 (R&D systems, Minneapolis, Minn.) was also treated with the enzymes that cleaved KGF under the same conditions as in FIG. 1. The results showed that trypsin, plasmin, and chymotrypsin all cleaved FGF-10 (19 kDa), but generated no stable cleavage fragment. Plasmin and trypsin did generate a transient ~16 kDa fragment that was apparently further degraded.

To determine if any stable FGF-10 fragment can be generated at a lower enzyme concentration, FGF-10 was treated with trypsin or plasmin at various concentrations under the conditions same as for KGF in FIGS. 3a and 3b. The result showed that at no enzyme concentration, the ~16 kDa cleavage product was more than 20% of the original FGF-10, while the complete cleavage of intact FGF-10 was reached over the enzyme concentration range used (FIGS. 3c and 3d). This is in sharp contrast to the cleavage of KGF by these two enzymes; the cleavage product (dN23KGF) accounted for at least 70% of the original KGF at enzyme concentrations where complete or nearly complete cleavage of the intact molecule was achieved (FIGS. 3a and 3b). This indicates that the ~16 kDa fragment of FGF-10 generated by trypsin or plasmin is further degraded with an efficiency close to the initial cleavage of the original FGF-10.

EXAMPLE 8

Cleavage of KGF by Wound Fluids and Inhibition with Plasmin Inhibitor Bdelin.

Full-thickness skin wounds were surgically made on the back (dorsum) of female piglets (40–45 pounds). Each wound was covered with saline-impregnated gauze sponge dressing followed by a non-permeable film dressing. Wound fluids were collected from the saline-impregnated gauze sponges removed during dressing change on day 2 and 4 post surgery. A total of 8 wound fluid samples from 4 different wounds were obtained and used. KGF (0.25 µg) was mixed with 5 µl of wound fluid in the presence or absence of Bdelin (Sigma Chemical Co. St. Louis, Mo.) at various concentrations in a 10 or 12.5 µl reaction volume. After incubation at 37° C. for 1 hr, the mixture was separated by gel electrophoresis and blotted onto an Immobilon-P membrane. The membrane was probed with goat anti-human KGF or rabbit anti-human KGF C-terminal peptide (see Example 2). The alkaline phosphatase-conjugated anti-goat IgG or -rabbit IgG and the enzyme substrate BCIP/NBT (5-bromo-4-chloro-3-indolyl phosphate/nitro blue tetrazolium) were used for detection. Densitometry analysis was performed as in Example 1.

The results showed that wound fluids cleaved KGF and generated a cleavage fragment identical in size to that (dN23KGF) by plasmin (FIG. 7a). The cleavage mainly occurred with day 4 wound fluids (FIG. 7a). Wounds at day 4 are at the early stage of the re-epithelialization process. The cleavage was inhibited by plasmin inhibitor bdelin in a dose-dependent manner and the amount of the cleavage fragment generated was reduced by 4.6 times with Bdelin at the highest amount used (2.5 µg) (FIG. 7b). This indicates that the enzyme responsible for KGF cleavage in wound fluids is plasmin and the fragment generated is dN23KGF. The cleavage fragment (dN23KGF) generated by wound fluids also reacted strongly with anti-KGF C-terminal peptide antibody.

Together, these results demonstrate that KGF can be cleaved by the plasmin in wound fluids, generating dN23KGF.

EXAMPLE 9

Cleavage of Native KGF by Plasmin.

Native KGF produced by mammalian cells is glycosylated and has a size (24–28 kDa) larger than the recombinant KGF. This experiment is to determine if plasmin also cleaves the native KGF isolated from murine 929 fibroblast cells, which are known to express KGF. Cells were cultured in DMEM with 5% FBS. Culture media were harvested and filtered through 0.2 µm filters. To each 500 ml of culture media, 0.5 ml heparin-agarose bead slurry (50%) was added. The media was kept at room temperature with shaking for 1 hr. Beads were washed with TN buffer and placed into a spin column to remove access buffer. The proteins bound to the beads were eluted with 1 M NaCl. The eluent was dialyzed against TN buffer. It was then treated with human plasmin as described above. Recombinant KGF was used as a control. Proteins were separated by gel electrophoresis and blotted onto an Immobilon-P membranes. The membrane was probed with rabbit anti-human KGF C-terminal peptide (see Example 2). The alkaline phosphatase-conjugated anti-rabbit IgG and the enzyme substrate BCIP/NBT (5-bromo-4-chloro-3-indolyl phosphate/nitro blue tetrazolium) were used for detection. Densitometry analysis was performed as in Example 1.

The native KGF did have a size (~26 kDa) larger than that of recombinant KGF as expected (FIG. 8). The enzyme digestion experiments showed that the native KGF was cleaved by plasmin, yielding a C-terminal cleavage fragment having a size identical to dN23KGF generated from recombinant KGF by the same enzyme.

EXAMPLE 10

Combination of KGF and Plasmin/Plasminogen or the Related for Treatment of Wounds or Other Disease Conditions: Formulation and Process.

The above described findings clearly indicate that the combination of KGF and plasmin/plasminogen or a related enzyme can be used to treat wounds or other disease conditions involving epithelial cells. The combination not only accelerates cell proliferation/differentiation, but also facilitates cell migration by clearing the fibrin clot and related extracellular matrix.

The combination is achieved by physically mixing KGF or a related growth factor selected from, but not limited to, those in list A at a concentration from 0.00001% to 0.1% (w/v) with plasmin/plasminogen or a related extracellular matrix-degrading protease enzyme selected from, but not limited to, those in List B at a concentration of 0.0001% to 1% (w/v) in a pharmaceutically acceptable carrier selected from, but not limited to, those in List C. The combination may further comprises a pharmaceutically acceptable thickener selected from, but not limited to, those in List D.

| List A: | List B: | List C: | List D: |
|---|---|---|---|
| EGF | Trypsin | Solutions | CMC |
| FGF-10 | tPA | Suspensions | Gelatin |
| HGF | uPA | Emulsions | HPMC |
| TGF-α | Streptokinase | Solid dosage forms | HEC |
| TGF-β | Staphylokinase | | Dextran |
| IGF-I | Metalloprotease | | Hyaluronic acid |
| aFGF | | | Pectin |
| | | | Alginate |
| | | | Chitosan |

Growth factors in List A, along with KGF, have all been shown to stimulate proliferation of epithelial cells. Most of them have also been shown to stimulate wound healing in animals and humans, including EGF, aFGF, KGF, FGF-10, and TGF-β. In human clinical studies, they have been used to treat various types of wounds including pressure ulcers, venous stasis ulcers, and burns. In animal studies (mouse, rat, rabbit or pig), full- or partial-thickness incisional or excisional wounds were most commonly used. In most cases, the growth factors were directly applied topically to the wound surface. Various growth factor doses were used with a typical range of 0.1 to 100 µg/cm$^2$. The growth factors were either applied in saline, buffered saline, a cream or a collagen sponge matrix. Some of the formulations contained a thickener. Before the treatment, wounds may be cleaned or debrided. After treatment, wounds may be covered with various types of dressings, including non-adhesive permeable or non-permeable film dressing, depending on the type of the wounds and the actual wound conditions. Various treatment schedules were used, including once daily and twice weekly. The whole treatment period may last over several weeks. The results were judged by various criteria, including re-epithelialization, granular tissue formation, angiogenesis, collagen content, wound breaking strength, and wound closure. Positive effect based on one or more of these criteria was achieved in many of animal and human studies using these growth factors. (Clark R. A. F. (ed.) The molecular and cellular biology of wound repair, Part II. Growth factor in soft tissue healing. pp 171–310. 1996. Plenum press. New York; Robson and Smith, Topical use of growth factors to enhance healing. In Cutaneous wound healing, Vincent F. (ed.) pp 379–398.2001. Martin Dunitz. London)

In List C, the solid dosage forms may include, but not limited to, tablets, capsules, powders, films, tapes, sponges, foams, pads, and other matrix or composite forms.

An active portion or fragment or a modified form of the growth factor or enzyme that retains all or a portion of the original activity may also be used in the combination. For example, dN23KGF may be used instead of KGF and miniplasmin/plasminogen may be used instead of plasmin/plasminogen. In addition, the enzyme in either an active form or an inactive form as a proenzyme may be used. It should be clear that if an active enzyme, such as plasmin, is used in combination with KGF, the dN23KGF will be generated in the formulation. On the other hand, if an inactive enzyme such as plasminogen is used, dN23KGF will not be generated.

One embodiment of the present invention pertains to a kit that holds a container with a growth factor (e.g. List A), and a container with an extracellular matrix-degrading protease enzyme or activator (e.g. List B). The contents of either container can either be in a carrier solution (e.g. List C or List D), or lyophilized with the carrier solution (e.g. List C or List D) in a third container for the user to reconstitute the components. A user of the kit could follow the protocol wherein the components of the kit are mixed and placed on an injury of an animal or human for the purpose of enhancing wound healing. Alternatively, the individual components of the kit can be placed on the injury in a tandem or sequential order.

Both the growth factors and the enzymes may be produced as native proteins by isolation from human or animal blood, tissues or cultured cells or as recombinant proteins by recombinant DNA techniques in prokaryotic or eukaryotic systems. Suitable methods for nucleic acid delivery for transformation of an organelle, a cell, a tissue or an organism for use with the current invention are believed to include virtually any method by which nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection, by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (U.S. Pat. No. 5,789,215, incorporated herein by reference); by electroporation (U.S. Pat. No. 5,384,253, incorporated herein by reference; by calcium phosphate precipitation; by using DEAE-dextran followed by polyethylene glycol; by direct sonic loading; by liposome mediated transfection and receptor-mediated transfection; by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (U.S. Pat. Nos. 4,684,611 and 4,952,500, each incorporated herein by reference); by desiccation/inhibition-mediated DNA uptake, and any combination of such methods. Through the application of techniques such as these, organelle(s), cell(s), tissue(s) or organism(s) may be stably or transiently transformed.

The combination of proteins or DNA vectors maybe formulated as a liquid or in a dried form. The combination may be administered subcutaneously, intramuscularly, intravenously, orally, topically, intranasally or by pulmonary delivery dependent on the disease conditions and formulations.

As the skilled artesian will know, the amount of either components in the combination may vary dependent on the disease conditions to be treated and route of administration in order to be clinically effective. Furthermore, instead of being formulated as a mixture or combination, the enzyme and growth factor may be formulated individually and mixed together just before use, or the enzyme is applied (such as topically, orally, parenterally, or by injection) first followed by the growth factor or vice versa. Even an alternate treatment scheme may be used with the growth factor treatment term, followed by the enzyme treatment term or vice versa. The time between the addition of either component can vary according to wound conditions and the status of healing.

The present invention includes the principle for the combination of a protease and a growth factor to achieve a synergistic effect on cellular functions. It should be appreciated by those of ordinary skill in the art that other embodiments may incorporate the concepts, methods, growth factors, proteases, and devices of the above description and examples. The description and examples contained herein are not intended to limit the scope of the invention, but are included for illustration purposes only. It is to be understood that other embodiments of the invention can be developed and fall within the spirit and scope of the invention and claims.

What is claimed is:

1. A composition comprising:
a mixture formed by mixing keratinocyte growth factor (KGF) and a protease enzyme selected from the group consisting of plasmin and plasminogen, wherein the mixture comprises at least a biologically active fragment of KGF.

2. The composition of claim 1, wherein the fibroblast growth factor protein has a concentration of from 0.00001% [w/v] to 0.1% [w/v], and the extracellular matrix-degrading protease enzyme has a concentration of from 0.0001 [w/v] to 1% [w/v].

3. The composition of claim 1 further comprising a carrier.

4. The composition of claim 3, wherein the carrier comprises water, a buffer, a saline solution, a thickener, an emulsion, or an ointment.

5. The composition of claim 3, wherein the composition and the carrier are lyophilized.

* * * * *